United States Patent
Sierad et al.

(10) Patent No.: US 10,022,225 B2
(45) Date of Patent: Jul. 17, 2018

(54) SELF-ADJUSTING TISSUE HOLDER

(71) Applicant: CLEMSON UNIVERSITY, Clemson, SC (US)

(72) Inventors: Leslie Sierad, Central, SC (US); Richard Pascal, Chapin, SC (US); Christopher deBorde, Longwood, FL (US); Dan Simionescu, Pendleton, SC (US); Agneta Simionescu, Pendleton, SC (US)

(73) Assignee: CLEMSON UNIVERSITY RESEARCH FOUNDATION, Clemson, SC (US)

( * ) Notice: Subject to any disclaimer, the term of this patent is extended or adjusted under 35 U.S.C. 154(b) by 123 days.

(21) Appl. No.: 14/807,407

(22) Filed: Jul. 23, 2015

(65) Prior Publication Data
US 2016/0022420 A1 Jan. 28, 2016

Related U.S. Application Data (60) Provisional application No. 62/028,064, filed on Jul. 23, 2014.

(51) Int. Cl.
*A61F 2/24* (2006.01)

(52) U.S. Cl.
CPC .................. *A61F 2/2472* (2013.01)

(58) Field of Classification Search
CPC .... A61F 2/2409; A61F 2/2412; A61F 2/2415; A61F 2/2427
See application file for complete search history.

(56) References Cited

U.S. PATENT DOCUMENTS

| | | | | |
|---|---|---|---|---|
| 5,488,789 A | * | 2/1996 | Religa | A61F 2/2412 38/102.2 |
| 5,607,470 A | * | 3/1997 | Milo | A61F 2/2409 623/2.39 |
| 5,800,531 A | * | 9/1998 | Cosgrove | A61F 2/2412 623/2.11 |
| 5,823,342 A | * | 10/1998 | Caudillo | A61F 2/0095 206/363 |
| 5,846,828 A | | 12/1998 | Peterson et al. | |
| 5,899,937 A | | 5/1999 | Golstein et al. | |
| 5,976,183 A | * | 11/1999 | Ritz | A61F 2/2409 623/2.11 |
| 6,121,042 A | | 9/2000 | Peterson et al. | |

(Continued)

OTHER PUBLICATIONS

Aleksieva, et al.; "Use of a special bioreactor for the cultivation of a new flexible polyurethane scaffold for aortic valve tissue engineering," *BioMedical Engineering Online*, 2012; 11, pp. 92. (20 pages).

(Continued)

*Primary Examiner* — Christopher M Koehler
(74) *Attorney, Agent, or Firm* — Dority & Manning, P.A.

(57) ABSTRACT

Tissue holders that can be used for gripping natural or synthetic heart valves are described. The tissue holder can include a clamping mechanism and a spring and can be self-adjusting with regard to pressure applied to the tissue gripped in the holder. The tissue holder can be removably attached to systems for processing the tissues and can provide completely hands-free processing of a tissue from development or excisement to implantation and/or completion of testing.

12 Claims, 10 Drawing Sheets

(56) References Cited

U.S. PATENT DOCUMENTS

| | | | |
|---|---|---|---|
| 6,126,007 | A | 10/2000 | Kari et al. |
| 6,214,043 | B1* | 4/2001 | Krueger ............... A61F 2/2427 |
| | | | 623/2.11 |
| 6,383,732 | B1 | 5/2002 | Stone |
| 6,409,758 | B2 | 6/2002 | Stobie et al. |
| 6,432,712 | B1 | 8/2002 | Wolfinbarger, Jr. |
| 6,652,583 | B2 | 11/2003 | Hopkins et al. |
| 6,702,852 | B2 | 3/2004 | Stobie et al. |
| 6,881,569 | B2 | 4/2005 | Perry et al. |
| 6,952,814 | B2 | 10/2005 | Joseph et al. |
| 6,964,682 | B2 | 11/2005 | Nguyen-Thien-Nhon et al. |
| 6,966,925 | B2 | 11/2005 | Stobie |
| 7,063,942 | B2 | 6/2006 | Dancu et al. |
| 7,112,218 | B2 | 9/2006 | McAllister et al. |
| 7,179,287 | B2 | 2/2007 | Wolfinbarger, Jr. |
| 7,378,271 | B2 | 5/2008 | Bader |
| 7,439,057 | B2 | 10/2008 | Frangos et al. |
| 7,498,412 | B2 | 3/2009 | Huang et al. |
| 7,504,258 | B2 | 3/2009 | McAllister et al. |
| 7,645,568 | B2 | 1/2010 | Stone |
| 7,658,763 | B2 | 2/2010 | Stobie |
| 7,691,046 | B2 | 4/2010 | Sullivan |
| 7,744,526 | B2 | 6/2010 | McAllister et al. |
| 7,753,840 | B2 | 7/2010 | Simionescu et al. |
| 7,754,232 | B2 | 7/2010 | Fisher et al. |
| 7,819,915 | B2* | 10/2010 | Stobie ............... A61F 2/2427 |
| | | | 623/2.11 |
| 7,851,200 | B2 | 12/2010 | More |
| 7,871,367 | B2 | 1/2011 | Anderson et al. |
| 8,230,717 | B2 | 7/2012 | Matonick |
| 8,308,629 | B2 | 11/2012 | Watschke et al. |
| 8,399,243 | B2 | 3/2013 | Bouten et al. |
| 8,491,457 | B2 | 7/2013 | Atala et al. |
| 8,609,415 | B2 | 12/2013 | Kortsmit et al. |
| 2006/0015177 | A1* | 1/2006 | Quest ............... A61F 2/2427 |
| | | | 623/2.11 |
| 2006/0136052 | A1* | 6/2006 | Vesely ............... A61F 2/2412 |
| | | | 623/2.18 |
| 2011/0167603 | A1* | 7/2011 | Vesely ............... A61F 2/2427 |
| | | | 29/221.6 |
| 2012/0290079 | A1* | 11/2012 | Murad ............... A61F 2/0095 |
| | | | 623/2.17 |
| 2014/0371842 | A1* | 12/2014 | Marquez ............. A61F 2/2445 |
| | | | 623/2.11 |

OTHER PUBLICATIONS

Baraki, et al.; "Orthotopic replacement of the aortic valve with decellularized allograft in a sheep model," *Biomaterials*; 2009; 30, pp. 6240-6246.

Barron et al., "Bioreactors for Cardiovascular Cell and Tissue Growth: A Review," *Annals of Biomedical Engineering*; 2003, 31, pp. 1017-1030.

Barzilla et al.; "Design and Validation of a Novel Splashing Bioreactor System for use in Mitral Valve Organ Culture," *Annals of Biomedical Engineering*, 2010; 38 (11), pp. 3280-3294.

Berry, et al.; "Bioreactors for Development of Tissue Engineered Heart Vavles," *Annals of Biomedical Engineering*, 2010; 38 (11), pp. 3272-3279.

Bilodeau, et al.; "Bioreactors for Tissue Engineering: Focus on Mechanical Constraint. A Comparative Review," *Tissue Engineering*, 2006; 12 (8), pp. 2367-2384.

Bowles, et al.; "Hydrodynamic Evaluation of a Bioreactor for Tissue Engineering Heart Valves," *Cardiovascular Engineering and Technology*, Mar. 2010; 1 (1), pp. 10-17.

Brazile, et al.; "On the Bending Properties of Porcine Mitral, Tricuspid, Aortic, and Pulmonary Valve Leaflets," *Journal of Long-Term Effects of Medical Implants*; (2014); pp. 41-53.

Breuer, et al.; "Application of Tissue-Engineering Principles toward the Development of a Semilunar Heart Valve Substitute," *Tissue Engineering*, 2004; 10 (1/2), pp. 1725-1738.

Butler, Ph.D. et al.; "Using Functional Tissue Engineering and Bioreactors to Mechanically Stimulate Tissue-Engineered Constructs," *Tissue Engineering*, 2009; 15 (4), pp. 741-751.

Caudle, N.; "The Matrix Reloaded," *Glimpse research and creative discovery*, Clemson University Magazine; Spring 2014, pp. 13-23.

Chow, et al.; "Mitigation of diabetes-related complications in implanted collagen and elastin scaffolds using matrix-binding polyphenol," *Biomaterials*, Jan. 2013; 34 (3), pp. 685-695.

Colazzo, et al.; "Extracellular matrix production by adipose-derived stem cells: implications for heart valve tissue engineering," *Biomaterials*, 2011; 32 (1), pp. 119-127.

DeBorde, et al.; "Development of a Tissue Engineered Mitral Valve Scaffold," ISACB Presentation, Apr. 2014; 1 page.

Durst, et al.; "Design and Physical Characterization of a Synchronous Multivalve Aortic Valve Culture System,"*Annals of Biomedical Engineering*; 2010, 38 (2), pp. 319-325.

Elman, et al.; "A comparison of adipose and bone marrow-derived mesenchymal stromal cell secreted factors in the treatment of systemic inflammation," *Journal of Inflammation (London)*, 2014; 11 (1), pp. 1-8. [doi:10.1186/1476-9255-11-1].

Engelmayr, Jr., et al.; "A Novel Flex-Stretch-Flow Bioreactor for the Study of Engineered Heart Valve Tissue Mechanobiology," *Annals of Biomedical Engineering*; 2008, 36 (5), pp. 700-712.

Flanagan, et al.; "The in vitro development of autologous fibrin-based tissue-engineered heart valves through optimized dynamic conditioning," *Biomaterials*; 2007, 28, pp. 3388-3397.

Geeslin, et al.; "Bioreactor for the reconstitution of a decellularized vascular matrix of biological origin," *Journal Biomedical Science and Engineering*; 2011, 4, pp. 435-442.

Gheewala, et al.; "Design and Mechanical Evaluation of a Physiological Mitral Valve Organ Culture System," *Cardiovascular Engineering and Technology*; 1 (2), pp. 123-131.

Goldstein, et al.; "Functional Tissue Engineering Requires Bioreactor Strategies," *Tissue Engineering: Part A*; 2009, 15 (4), pp. 739-740.

Grande-Allen, et al.; "The heterogenneous biomechanics and mechanobiology of the mitral valve: implications for tissue engineering," *Curr. Cardiol. Reports*, 2011; 13 (2), pp. 113-120.

Hildebrand, et al.; "Design and Hydrodynamic Evaluation of a Novel Pulsatile Bioreactor for Biologically Active Heart Valves," *Annals of Biomedical Engineering*; 2004, 32 (8), pp. 1039-1049.

Hildebrand; "Design and Evaluation of a Novel Pulsatile Bioreactor for Biologically Active Heart Valves" *Paper Submitted to Graduate Faculty of School of Engineering—Univ. of Pittsburgh*; 2003, 187 pages.

Hoerstrup, et al.; "Tissue engineering of small caliber vascular grafts," *European Journal of Cardio-thoracic Surgery*; 2001, 20, pp. 164-169.

Hoerstrup, M.D., et al.; "Functional Living Trileaflet Heart Valves Grown in Vitro," *American Heart Association Inc.*; 2000, available at http://www.circulationaha.org. (6 pages).

Kaasi, et al.; "Using a VAD-Based Bioreactor to Host a Tissue Engineered Heart Valve," 21° *Congresso Brasileiro de Engenharia Biomédica*; (DATE Unknown), ISBN: 978-85-60064-13-7 (4 pages).

Karim, et al.; "The Cariovascular Tissue-Reactor: A Novel Device for the Engineering of Heart Valves," *Artificial Organs*; 2006, 30 (10), pp. 809-814.

Kennamer, Allison R.; "Interstitial Cell Seeding and Dynamic Conditioning of Aortic heart Valve Scaffolds," A Thesis—Graduate School, Clemson University; Dec. 2013; 77 pages.

Konduri, et al.; "Normal Physiological Conditions Maintain the Biological Characteristics of Porcine Aortic Heart Valves: An Ex Vivo Organ Culture Study," *Annals of Biomedical Engineering*; 2005, 33 (9), pp. 1158-1166.

Lee, M.S., et al.; "Endothelialization of Heart Valve Matrix Using a Computer-Assisted Pulsatile Bioreactor," *Tissue Engineering*; 2009, 15 (4), pp. 807-814.

Leo, et al.; "A Comparison of Flow Field Structures of Two Tri-Leaflet Polymeric Heart Valves," *Annals of Biomedical Engineering*; 2005, 33 (4), pp. 429-443.

(56) References Cited

OTHER PUBLICATIONS

Leo, et al.; "Fluid Dynamic Assessment of Three Polymeric Heart Valves using Particle Image Velocimetry,"*Annals of Biomedical Engineering*; 2006, 34 (6), pp. 936-952.
Liao, et al.; "Effects of decellularization on mechanical and structural properties of the porcine aortic valve leaflets," *Biomaterials*; Mar. 2008; 29 (8): pp. 1065-1074.
Lichtenberg, et al.; "In vitro re-endothelialization of detergent decllularized heart valves under simulted physiological dynamic conditions," *Biomaterials*; 2006, 27, pp. 4221-4229.
Lieber, et al.; "Design of Miniature Tissue Culture System to Culture Mouse Heart Valves," *Annals of Biomedical Engineering*; 2010, 38 (3), pp. 674-682.
Martin, et al.; "Bioreactors for tissue mass culture: Design, characterization, and recent advances," *Biomaterials*; 2005, 26, pp. 7481-7503.
Martin, et al.; "The role of bioreactors in tissue engineering," *Trends in Biotechnology*; 2004, 22 (2), 7 pages.
Miller; "Design and Development of a Novel Bioreactor for Tissue Engineered Heart Valves," *A Thesis Presentation—Arizona State University*; 2002, 136 pages.
Mol, et al.; "Tissue Engineering of Human Heart Valve Leaflets: A Novel Bioreactor for a Strain-Based Conditioning Approach," *Annals of Biomedical Engineering*; 2005, 33 (12), pp. 1778-1788.
Montoya, et al.; "Preparation of Ex Vivo-Based Biomaterials Using Convective Flow Decellularization," *Tissue Engineering, Part C*, 2009; 15 (2), pp. 191-193.
Morsi, PhD., et al.; "Development of a novel pulsatile bioreactor for tissue culture," *Jrnl. Artif. Organs*; 2007, 10, pp. 109-114.
Narita, M.D., et al.; "Novel Pulse Duplicating Bioreactor System for Tissue-Engineered Vascular Construct," *Tissue Engineering*; 2004, 10 (7/8), pp. 1224-1233.
Pascal, et al.; "Systems to Facilitate Adult Stem Cell Seeding of Aortic Heart Valve Scaffolds," Poster; *Department of Bioengineering: Clemson University*; (Nov. 15, 2012), 1 page.
Paz, et al.; "Tissue Engineered Trachea Using Decellularized Aorta," *Journal of Bioengineering& Biomedical Science*, 2011; S2:001. DOI: 10.4172/2155-9538.S2-001. (7 pages).
Ratcliffe, et al.; "Bioreactors and Bioprocessing for Tissue Engineering," *Ann. N.Y. Acad. Sci.*; 2002, 961, pp. 210-215.
Ruel, et al.; "A New Bioreactor for the Development of Tissue-Engineered Heart Valves," *Annals of Biomedical Engineering*; 2009, 37 (4), pp. 674-681.
Sarkar, et al.; "Addressing thrombogenicity in vascular graft construction,"*Journal of Biomedical Materials Research, Part B Applied Biomaterials*, 2007; 82 (1), pp. 100-108.
Sauer et al; "Thoughts and Progress,"*Artifical Organs*; 2002, 26(8), pp. 703-733.
Schenke-Layland, et al.; "Complete dynamic repopulation of decellularized heart valves by application of defined physical signals—an in vitro study," *Cardiovascular Research*; 2003, 60, pp. 497-509.
Schliecher, et al.; "Simplified Pulse Reactor for Real-Time Long-Term In Vitro Testing of Biological Heart Valves," *Annals of Biomedical Engineering*; 2010, 38 (5), pp. 1919-1927.
Sierad, et al.; "Design and Testing of a Pulsatile Conditioning System for Dynamic Endothelialization of Polyphenol-Stabilized Tissue Engineered heart Vavles,"*Cardiovascular Engineering and Technology*; (Jun. 2010) vol. 1, No. 2, pp. 138-153.
Sierad, et al.; "Surface Modification, Endothelial Cell Coating, and Bioreactor Testing of Mechanical Heart Valves" PowerPoint— Clemson University, Clemson SC 29634; (2013); pp. 1-22.
Sierad, et al.; "Surface Modification, Endothelial Cell Coating, and Bioreactor Testing of Mechanical Heart Valves," Article; Clemson University, Clemson SC 29634; (May 2012); 1 page.
Sierad, et al.; "Surface Modification, Endothelial Cell Coating, and Bioreactor Testing of Mechanical Heart Valves," Poster Presentation; Clemson University, Clemson SC 29634; (2013); 1 page.
Sierad, et al.; "Bioreactor Technologies for Clinical Translation of Tissue Engineered Heart Valves," ISACB Article Presentation; Clemson University, Clemson SC 29634; (Apr. 2, 2014); 2 pages.
Sierad, L.N.; "A Pulsatile Bioreactor for Conditioning Tissue Engineered heart Valves,"*A Thesis Presented to Graduate School of Clemson University*, May 2009; 95 pages.
Simionescu; "Form Follows Function: Advances in Trilayered Structure Replication for Aortic Heart Valve Tissue Engineering," *Journal of Healthcare Engineering*; 2012, 3, pp. 179-202.
Sodian, M.D., et al.; "New Pulsatile Bioreactor for Fabrication of Tissue-Engineered Patches," *J. Biomed. Mater. Res.*; 2001, 58, pp. 401-405.
Sodian, M.D., et al.; "Tissue Engineering Bioreactors: A New Combined Cell-Seeding and Perfusion System for Vascular Tissue Engineering," *Tissue Engineering*; 2002, 8(5), pp. 863-872.
Sodian, M.D., et al.; "Tissue Engineering of a Trileaflet Heart Valve—Early In Vitro Experiences with a Combined Polymer," *Tissue Engineering*; 1999, 5 (5), pp. 489-494.
Sodian, M.D., et al.;"Tissue Engineering of Heart Valves: In Vitro Experiences," *Ann. Thoracic Surgery*; 2000, 70, pp. 140-144.
Sodian, M.D., et al.; "Tissue-Engineering Bioreactors: A New Combined Cell-Seeding and Perfusion System for Vascular Tissue Engineering," *Tissue Engineering*; 2002, 8 (5), pp. 863-873.
Tedder, et al., "Stabilized Collagen Scaffolds for Heart Valve Tissue Engineering," *Tissue Engineering; Part A*; 2009, 15 (6), pp. 1257-1268.
Tedder, et al.; "Assembly and Testing of Stem Cell-Seeded Layered Collagen Constructs for Heart Valve Tissue Engineering," *Tissue Engineering: Part A*; 2011, 17, 1 and 2, pp. 25-38.
Warnock, et al.; "Design of a Sterile Organ Culture System for the Ex Vivo Study of Aortic Heart Valves," *Journal of Biomechanical Engineering*; Oct. 2005, 127, pp. 857-861.
Wendt, et al.; "Potential and Bottlenecks of Bioreactors in 3D Cell Culture and Tissue Manufacturing," *Advanced Materials*; 2009, 21, pp. 3352-3367.
Weston, et al.; "Biosynthetic Activity in Heart Valve Leaflets in Response to In Vitro Flow Environments," *Annals of Biomedical Engineering*; 2001, 29, pp. 752-763.
Zeltinger, PhD., et al.; "Development and Characterization of Tissue-Engineered Aortic Valves," *Tissue Engineering*; 2001, 7 (1), pp. 9-22.
Ziegelmueller, et al.; "Optical Monitioring During Bioreactor Conditioning of Tissue-Engineered Heart Valves," *Tissue Engineering*; 2010, 56, pp. 228-231.
Zou, PhD., et al.; "Mechanical Evaluation of Decellularized Porcine Thoracic Aorta," *Journal of Surgical Research*; 2012, 175, pp. 359-368.

\* cited by examiner

SELF-ADJUSTING TISSUE HOLDER

CROSS REFERENCE TO RELATED APPLICATION

This application claims filing benefit of U.S. Provisional Patent Application Ser. No. 62/028,064 having a filing date of Jul. 23, 2014, which is incorporated herein in its entirety.

STATEMENT AS TO RIGHTS, TO INVENTIONS MADE UNDER FEDERALLY SPONSORED RESEARCH

This invention was made with Government support under Grant No. RO1 HL 093399 awarded by the National Institutes of Health. The Government has certain rights in the invention.

BACKGROUND

The overall prevalence of heart valve disease in the United States, adjusted to the 2000 population, was estimated at that time to be 2.5%, with about 99,000 heart valve operations yearly. By 2011, it was estimated that roughly four million people in the United States were diagnosed annually with a heart valve disorder. Often, the only solution for degenerated or calcified heart valves is replacement of the entire valve, which up to now has been either a bioprosthetic or mechanical valve.

The first designs of replacement heart valves were for mechanical models, with major breakthroughs occurring in the 1950's and 1960's. The ball-in-cage design prevailed for many years until the tilting disc's emergence. The pyrolytic carbon bileaflet valve was designed in the 1970's and became the 'gold standard' for mechanical valve replacement. Since St. Jude Medical introduced the pyrolytic carbon valve much of the innovation in this area has come to a halt and only minor features of mechanical valves have evolved over the last forty years.

Although mechanical valves are the most durable solution for heart valve replacements (typically said to last for 20-30 years) thrombogenicity of the artificial surfaces remains a cause for much concern. Not only are the devices non-biological, they also introduce turbulent flow regimes. The turbulence can activate platelets which in turn initiate the formation of thrombi. To prevent this from occurring, patients are put on life-long anticoagulant therapy that involves the administration of Warfarin. Unfortunately, because Warfarin decreases the blood's ability to coagulate on the valve it also prevents coagulation systemically, leaving the patient vulnerable to major bleeding events. The reliance upon an expensive drug therapy and the necessity of close patient monitoring is undesirable and the main factor that has kept mechanical valve replacement out of developing countries.

A solution to the increased thrombogenicity of mechanical valves was the advent of bioprosthetic valve (BPV) technology. These valves are made from either porcine aortic valves or bovine pericardium that has been chemically fixed, cross-linking the tissue and masking the antigens present in the xenogeneic materials. BPVs are predicted to last 10-15 years, which is a lower expectation than that of mechanical valves. In addition, it has been found that after 15 years all-cause mortality is lower for patients implanted with mechanical valves as compared to BPVs. Although the mechanical valve has been shown to be more durable and can be projected to last longer, the BPV is still the best choice for those patients who cannot be put on anticoagulant regimes. In addition, certain patient populations preferably receive certain valves. For example elderly patients (65 years and older) typically receive BPVs because of expected life span and the reduced chance for calcification, and younger patients/children receive mechanical valves due to the decreased number of expected replacements required.

More recently, tissue engineering approaches have been developed that seek to make curative solutions for patients who are seeking long-term treatment of disease and tissue degeneration. The constructs that are being researched and tested will not simply compensate for the damaged tissue; the aim is to create living tissue that can be implanted into a human that will, from that point on, grow and remodel. Ideally, a tissue engineered heart valve will resemble both the size and shape of the native valve; be durable and fully functioning with good hemodynamics; be non-immunogenic, non-inflammatory, non-thrombogenic, and non-obstructive; respond to mechanical and biological cues appropriately; grow in size with the recipient; and will adapt to changing conditions throughout the life of the recipient and valve.

Whether for study or implantation, natural and synthetic heart valve tissue BHV and engineered tissue) is generally subjected to multiple treatment regimes. For instance, xenograft valve tissue must be decellularized to remove the native cells prior to either testing or implant. In addition, mechanical testing by use of a conditioning system can be carried out to examine and alter tissue strength or to ensure suitable strength prior to implant. Seeding of natural or synthetic scaffolds can also be carried out in development of new valves and/or to encourage integration with a recipient's natural tissue following implantation.

It has been common to secure valve tissue during the various treatment regimens by temporarily suturing or clipping the tissue to mounting rings. Unfortunately, physically attaching the tissue to the holding device can damage the tissue and cause mechanical weakening of the tissue. Moreover, securement systems generally do not provide a method for securing the tissue with a tight seal, and fluid leakage around the tissue during the treatment protocols can prevent effective conditioning and/or testing. Additionally, the tissue characteristics can change during treatment. For instance decellularization can lead to a loss of tissue volume, and presently known systems do not account for the physical changes of the tissue associated with a volume loss. Thus, with present systems, the tissue can become loose in/on the holder and/or leaks can form between the tissue and the holder as decellularization takes place.

What is needed in the art is a tissue holder that can effectively grip tissue during conditioning and/or testing. For instance, a heart valve tissue holder that can provide for totally hands-free and secure retention during multiple treatment regimens would be of great benefit for natural or synthetic heart valve tissue for research and development protocols as well as for implantation protocols.

SUMMARY

According to one embodiment, disclosed is a tissue holder. In one particular embodiment, the tissue holder can be a heart valve tissue holder. The tissue holder can include a first holding plate and a second holding plate. The first holding plate has a first side and a second side and a primary opening that passes from the first side to the second side of the first holding plate. The second holding plate also has a first side and a second side and a primary opening that passes from the first side to the second side of the second holding plate. The first and second holding plates are alignable with one another such that upon alignment the second side of the first holding plate is adjacent to the first side of the second holding plate and the primary openings of the two holding plates align with one another.

The tissue holder can also include a clamping mechanism. When tightened the clamping mechanism can apply a clamping force between the first side of the first holding plate and the second side of the second holding plate when the two holding plates are aligned with one another.

In addition, the tissue holder can include a spring. The spring can be held between the clamping mechanism and either the first holding plate or the second holding plate. During use, the spring can maintain the clamping force between the two holding plates.

Methods for utilizing the tissue holder are also disclosed. For instance a method can include locating a portion of a tissue on a surface of the first holding plate, for example on the second side of the first holding plate. Following, the second holding plate can be aligned with the first holding plate such that the tissue portion is between the first holding plate and the second holding plate and the primary openings of the two holding plates are axially aligned. The clamping mechanism can then be tightened thereby gripping the tissue portion between the first and second holding plates. The spring of the tissue holder can serve to maintain the clamping pressure on the tissue portion, for instance following decellularization of the tissue.

In one embodiment, the tissue holder can be used to hold heart valve tissue with the tissue portion held between the holding plates being, e.g., a ventricular portion of a heart valve. In this embodiment, the heart valve can be held within the aligned openings of the two holding plates and, when present, an aortic root of the heart valve can extend away from the heart valve. The tissue holder can optionally also include a support stand to support the aortic root.

BRIEF DESCRIPTION OF THE FIGURES

The present disclosure may be better understood with reference to the figures including:

FIG. 4 illustrates several views of a lower casing piece of a tissue holder including a bottom view (FIG. 4A) a perspective view (FIG. 4B), a top view (FIG. 4C), a schematic bottom view (FIG. 4D) and a sectional side view (FIG. 4E).

FIG. 5 illustrates a schematic top view (FIG. 5A) and a sectional view (FIG. 5B) of an upper casing piece of a tissue holder.

FIG. 13 illustrates the heart valve and associated tissue held in the device including a top view (FIG. 13A) and a bottom view (FIG. 13B).

Repeat use of reference characters in the present specification and drawings is intended to represent the same or analogous features or elements of the present disclosure.

DETAILED DESCRIPTION

Reference will now be made in detail to various embodiments of the disclosure, one or more examples of which are illustrated in the accompanying drawings. Each example is provided by way of explanation of the subject matter, not limitation thereof. In fact, it will be apparent to those skilled in the art that various modifications and variations can be made in the present disclosure without departing from the scope or spirit of the subject matter. For instance, features illustrated or described as part of one embodiment, can be used on another embodiment to yield a still further embodiment.

The present disclosure relates generally to tissue holders and, in one particular embodiment, to tissue holders for gripping natural or synthetic heart valves. Beneficially, the tissue holder can be self-adjusting with regard to pressure applied to the tissue gripped in the holder. In this embodiment, the tissue holder can firmly grip a tissue sample throughout a procedure such as decellularization, seeding, or conditioning during which the physical characteristics (e.g., thickness) of the gripped tissue can change. As the tissue characteristics vary during the treatment protocol, the self-adjusting capability of the tissue holder can allow for the clamping force on the gripped tissue to be maintained and the tissue can be securely gripped in the holder throughout the procedure.

As utilized herein, the term "tissue" generally refers to an organization of one or more components that can support and interact with living cells. A tissue can be a natural tissue obtained from a natural source (e.g., human or animal-derived tissue), and can include natural structural components such as the structural proteins collagen, elastin, laminin, etc. Alternatively, a tissue can be a synthetic tissue, in which the structural components can include synthetically formed materials, e.g., hydrogel networks and fibers, etc. that can include synthetic polymers. A synthetic tissue can also include natural polymers, such as collagen, alginates, etc., that have been processed in some fashion to form the synthetic tissue. The cells supported on/in a tissue can be the cells that are naturally present in a natural tissue or can be cells that are seeded on the natural or synthetic tissue for study and/or implantation in a living subject. The term "tissue" can refer to both the acellular structural scaffolding material as well as the structural scaffolding material in conjunction with cells.

The self-adjusting characteristics of the tissue holder can provide a route to firmly grip a tissue during multiple different regimens. In addition, the tissue holder can be designed to fit with different treatment devices and systems.

For instance, the tissue holder can be utilized in conjunction with a decellularization device and system during which the tissue gripped in the holder can be decellularized. Following decellularization, the tissue holder can be moved to a cell seeding device and/or a bioreactor where the tissue gripped in the device can be subjected to strength testing, cell seeding etc. Thus, the tissue can be subjected to multiple different regimens in multiple different systems without removal from the tissue holder. This can provide for totally hands-free treatment of a tissue from initial development (in the case of a synthetic tissue) or from excisernent (in the case of a natural tissue) to either implantation or testing completion.

Figure 1:
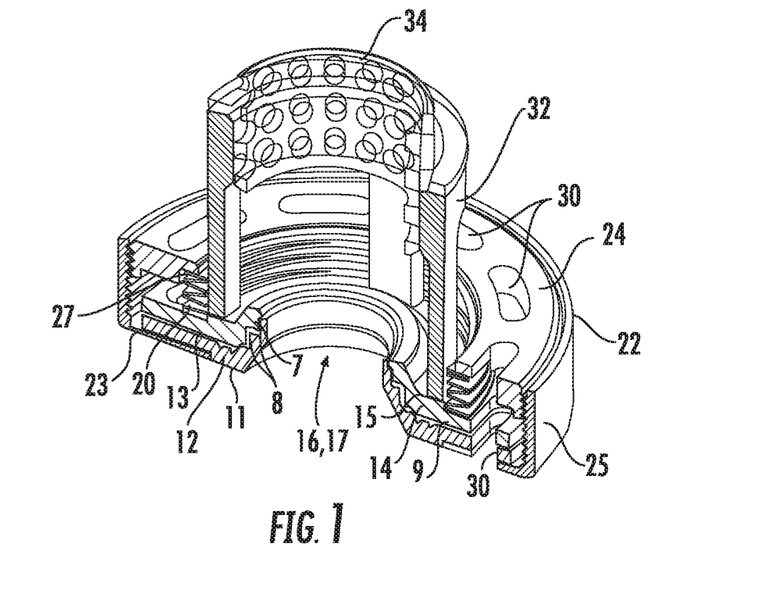
FIG. 1 is a schematic of a sectional perspective view of one embodiment of a tissue holder as disclosed herein.

One embodiment of a tissue holder 10 is illustrated in the cut-away sectional view of FIG. 1. In this embodiment, the tissue holder includes a first holding plate 12 and a second holding plate 14.

The first holding plate 12 has a first side 11 and a second side 13 and the second holding plate 14 has a first side 9 and a second side 15. In addition, the first holding plate 12 defines a primary opening 16 therethrough that passes from the first side 11 to the second side 13 of the first plate 12. Likewise the second holding plate 14 defines a primary opening 17 therethrough that passes from the first side 9 to the second side 15 of the second plate 14. The first and second plates 12, 14 can be located adjacent to one another such that when they are aligned as shown in FIG. 1, the primary openings 16 and 17 are axially aligned with one another.

During use, a tissue portion can be clamped between the adjacent sides of the two holding plates, e.g., between the second side 13 of the first plate 12 and the first side 9 of the second plate 14.

To improve the grip of the tissue holder 10 on the tissue held between the holding plates 12, 14, one or both of the plates can include one or more three dimensional features such as bumps, ridges, indentations, etc. on the side of the plate that will contact the tissue. For example, as shown in FIG. 1, the second side 13 of the first plate 12 can include a series of ridges 8 defined on the second side 13. In addition, the second plate 14 can define a series of impressions 7 that can mate with the ridges 8 when the holding plates 12, 14 are aligned. The mated features can increase the gripping force between the two plates. It should be understood, however, that while features on one side of a plate can be paired with mated features on the facing plate, mated features are not a requirement of the tissue holder. For example, the second side 13 of the first plate 12 can define three-dimensional features such as ridges, bumps, etc. and the first side 9 of the second plate 14 can be substantially flat, such that the tissue sample is tightly held between the features of the first plate 12 and the flatter surface of the second plate 14.

Components of a tissue holder can be formed of polymeric materials, ceramic materials, metals, metal alloys, or any other formable material. For instance, the first plate 12 and the second plate 14 can both be formed of polymeric materials such as polyethylene (including high density polyethylene, ultrahigh molecular weight polyethylene, etc.), polysiloxanes, polyurethanes, polyvinyl chloride, polyacrylates, and so forth. Polymeric materials can be shaped according to known methodology, e.g., injection molding processes, 3-D printing, etc., to form one or more components of a tissue holder. The first plate 12 and the second plate can optionally be formed of other materials, however, such as ceramic materials (e.g., aluminum oxide, zirconia, etc.), or metals or metal alloys (e.g., stainless steel, cobalt alloys, titanium alloys, etc.) that can be molded or shaped according to standard methodology.

In addition, the different components of a tissue holder can be formed of the same or different materials. For example, in the embodiment of FIG. 1, the first holding plate 12 and the second holding plate 14 can both be formed of the same material, e.g., a polymeric material. In other embodiments, such as that of embodiment of FIG. 2, the first holding plate 212 can be formed of a metal or metal alloy and the second holding plate 214 can be formed of a polymeric material. Any combination of suitable materials is encompassed herein.

The dimensions of a tissue holder can vary generally depending upon the tissue type that will be utilized with the holder. For instance, when a tissue holder is intended for use with heart valve tissue, the cross-sectional dimension of the tissue holder can generally be from about 1 inch to about 3 inches. The device cross section can be larger or smaller, however, as desired.

Similarly, the cross-sectional dimension of the primary openings 16, 17 of the aligned plates 12, 14 can vary, depending on the tissue type and size to be gripped by the holder. Moreover, the aligned openings need not have the same cross sectional dimension as one another. For instance, as shown in FIG. 1, the first and second holding plates 12, 14, are nested at the openings 16, 17, with the diameter of the opening 17 of the second plate 14 being smaller than the opening 16 of the first plate 12.

Figure 16:
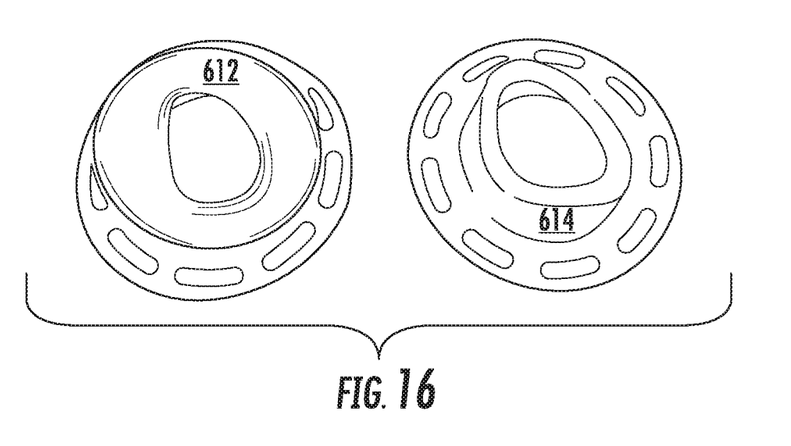
FIG. 16 presents a top view of holding plates for a tissue holder as described herein.
Figure 17:
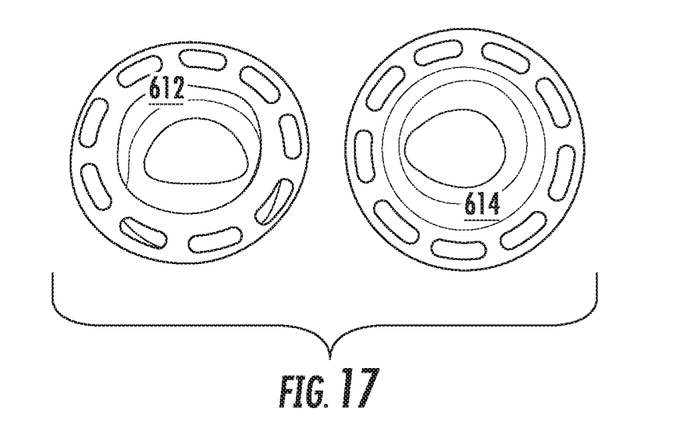
FIG. 17 presents a bottom view of the holding plates of FIG. 16.
Figure 18:
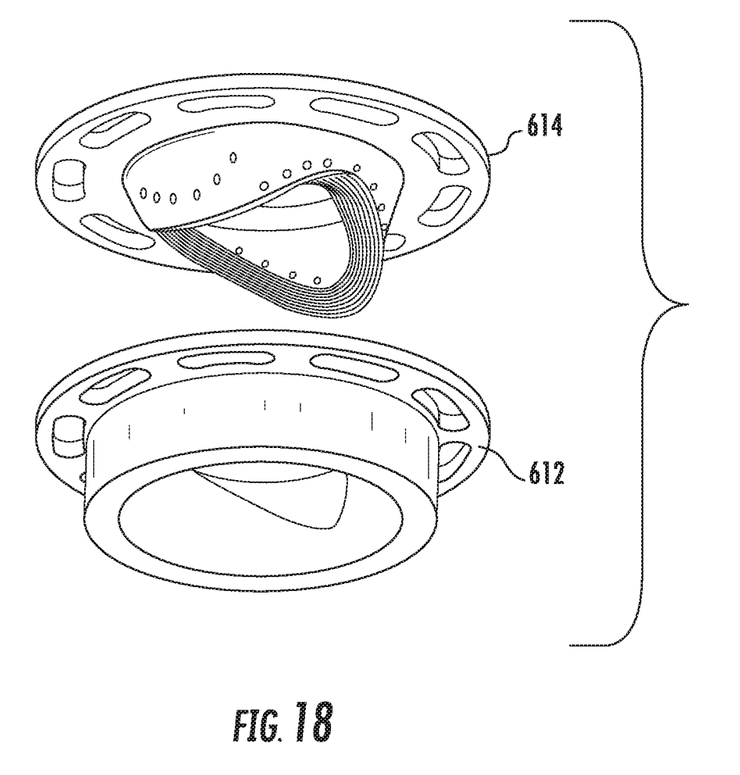
FIG. 18 presents a perspective view of the holding plates of FIG. 16

The device can also be provided with multiple plates that can provide various sizes and shapes of openings for treatment of different tissue types and sizes. By way of example, the tissue holder of FIG. 2 includes a first plate 212 and a second plate 214. In this embodiment, the primary opening 217 of the second plate 214 is larger than the primary opening 216 of the first plate 212. The size of the smaller of the two openings (e.g., opening 216) will be the limiting size for determining the size of the tissue gripped by the tissue holder. The holder can optionally include other first and second plates with larger or smaller openings or differently shaped openings that can be utilized alternatively to the first and/or second plates. For example, FIG. 16, FIG. 17, and FIG. 18 illustrate holding plates including a non-circular primary opening. FIG. 16 illustrates a top view of a first holding plate 612 and a second holding plate 614, FIG. 17 presents a bottom view of the holding plates 612, 614, and FIG. 18 presents perspective views of the holding plates 612, 614. As can be seen, the primary openings of these holding plates are not round. In addition plates 612, 614 include suture holes that can be used to further stabilize a tissue held by the plates 612, 614. Additional stabilization capabilities, such as suture holes, can be included in any holding plate of a system. By switching a holding plate having one opening size or shape for a plate having a different opening size, the tissue holder can be used to grip a tissue of a different size or shape, for instance a mitral valve tissue segment. The diameter of the primary openings (or largest cross-sectional dimension in the case of a non-circular opening) can generally be from about 0.5 inches to about 1.5 inches when considering use for heart valve tissues. This dimension can vary, however, for instance for other tissue types.

The thickness of the first and second holding plates is generally not limited. In one embodiment, for example, the first and second plates can have a thickness from the first side to the second side of from about 0.05 inches to about 0.25 inches, or from about 0.1 inches to about 0.15 inches in some embodiments.

The tissue holder 10 can also include a spring 20 that applies a force to the first plate 14. In other embodiments, a spring may be located in conjunction with the second plate 12 rather than the first plate 14. The spring 20 is illustrated as a single coiled spring, but any type or number of springs can be utilized. For instance, a single or multiple leaf springs can be held against a plate of the holder or multiple coiled springs can be utilized, each held against a holding plate of the holder such that the spring exerts force on the plate. The force exerted on the plate by the spring can vary depending primarily on the tissue type to be held. In one embodiment, for example, the spring can exert a load of between about 5 pounds-force ($lb_f$) and about 100 $lb_f$ at the working surface. In embodiments in which the tissue holder does not include the spring, the tissue holder can be manually tightened or loosened as needed to maintain desired pressure on the tissue held between the holding plates.

The spring can be formed of any material, e.g., any ceramic, polymeric, metal, or metal alloy as is generally known that can exert a force against one of the two holding plates by use of a clamping mechanism. The clamping mechanism can use any method of clamping, e.g., clips, screws, etc. In the illustrated embodiment, the clamping mechanism is threaded and the gripping forces applied to a tissue held between the two plates can be increased and decreased as needed by tightening or loosening of the threaded clamping mechanism.

Figure 4A:
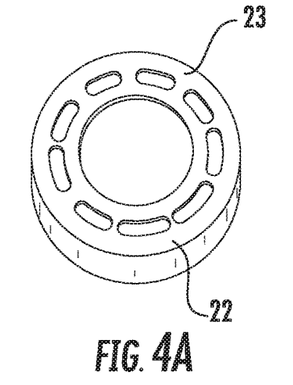
Figure 4B:
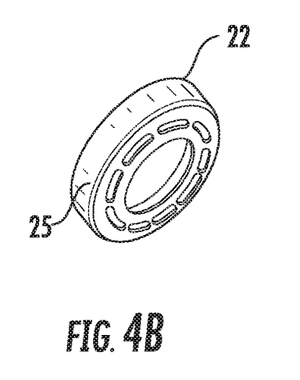
Figure 4C:
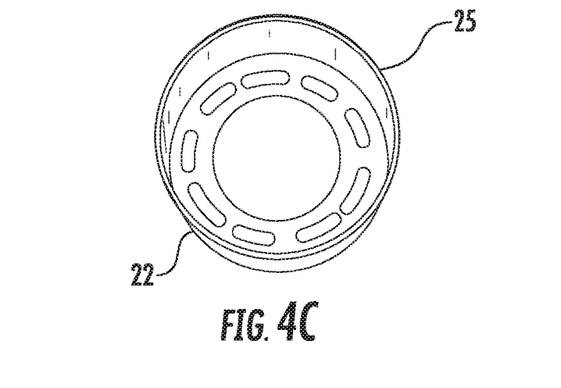
Figure 4D:
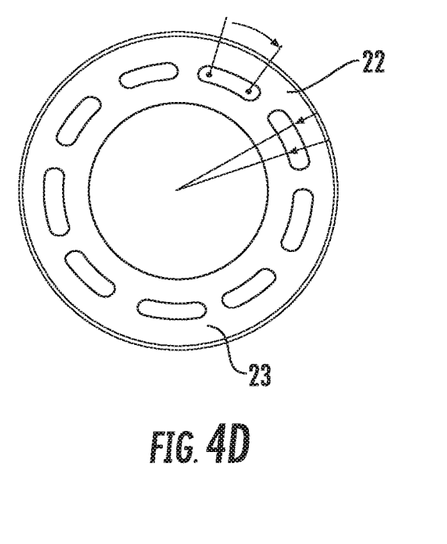
Figure 4E:
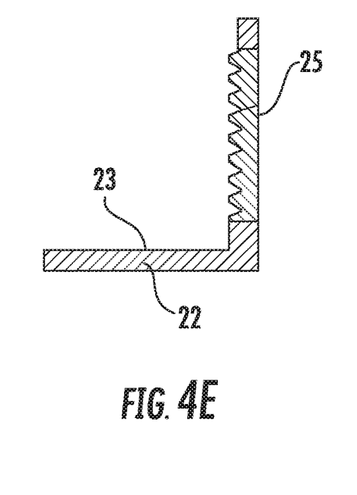

In the embodiment illustrated in FIG. 1, the threaded clamping mechanism includes a first casing 22 and a second casing 24. Several views of the first casing 22 are shown in FIG. 4 including a bottom perspective view (FIG. 4A), a side perspective view (FIG. 4B), a top perspective view (FIG. 4C), a bottom view (FIG. 4D) and a sectional side view (FIG. 4E). The first casing 22 includes a base 23 and a side 25 that is threaded on an interior surface, as shown. Upon assembly, the first plate 12 can be seated in the first casing 22 with the first side 11 of the first plate 12 adjacent to the base 23 of the first casing 22. The first casing can be formed of a material that can support and maintain the threads of the casing with repeated use, e.g., a ceramic, polymeric, metal or metal alloy.

Figure 5A:
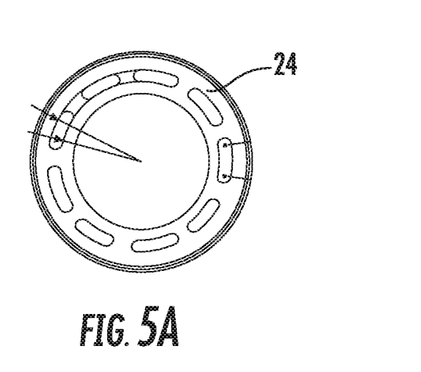
Figure 5B:
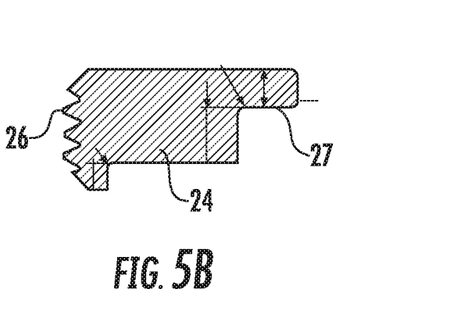

FIG. 5 illustrates a top view (FIG. 5A) and a sectional view (FIG. 5B) of the second casing 24. Second casing 24 includes a surface 27 that, upon assembly of the tissue holder 10 will contact one end of the spring 20 as shown in FIG. 1. In this particular embodiment, the other end of the spring 20 abuts the second side 15 of the second plate 14 to apply pressure to the second plate 14 when compressed. The second casing 24 includes an external threaded side 26 that can partner with the internal threaded side 25 of the first casing 22 and function as a clamping mechanism for the tissue holder 10 when tightened together.

Once the clamping mechanism is tightened via the partnered threaded surfaces of the first casing 22 and the second casing 24, a tissue can be firmly held between the first holding plate 12 and the second holding plate 14. The spring 20 located between the second casing 24 and the second plate 14 applies pressure to a tissue held in the device once the first and second casings 22, 24 are attached to one another at the threaded surfaces. This pressure can be maintained within a relatively narrow range and can be automatically adjusted by the spring even upon changes to the tissue clamped in the tissue holder.

Figure 2:
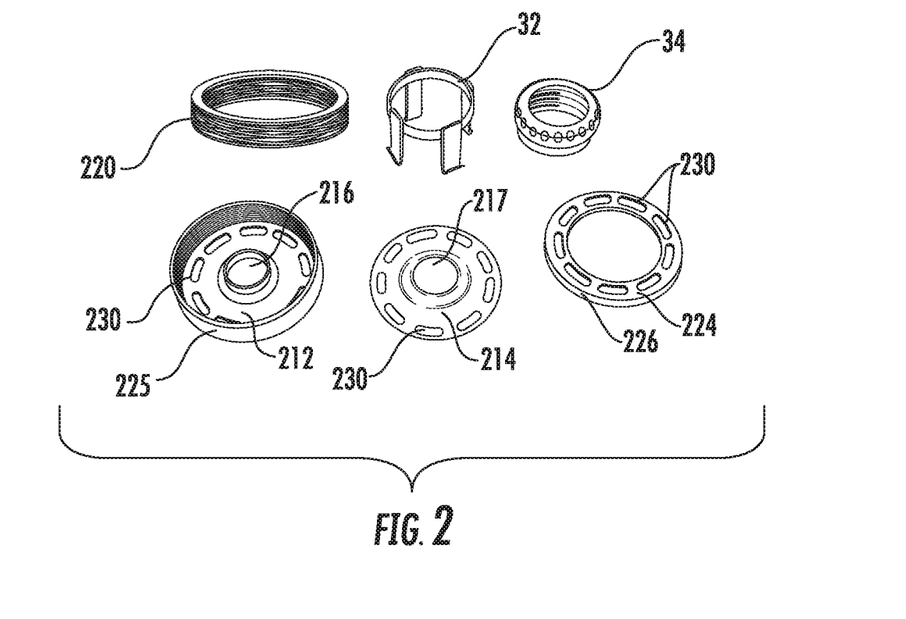
FIG. 2 illustrates several pieces of a disassembled tissue holder.

In one embodiment one or more sections of a clamping mechanism can be integrated with other components of the tissue holder. For example, as illustrated in FIG. 2, the first holding plate 212 can include a side 225 that has a threaded interior surface. In this embodiment, the casing 224, is similar to that of the second casing 24 of FIG. 1. However, in this embodiment the first holding plate 212 can be directly attached to the casing 224 via the paired threaded sides of the two components. The exterior threaded side 226 of the casing 224 can be paired to the interior threaded side 225 of the first plate 212. In addition, the second holding plate 214 can be aligned with the first holding plate 212 with the primary openings 216, 217 axially aligned and a tissue sample (not shown in FIG. 2), gripped between the first plate 212 and the second plate 214. A spring (220) can be located between the second plate 214 and the casing 224 and upon tightening the casing 224 to the first plate 212 via the threads the tissue sample can be tightly gripped by the device.

As seen in FIG. 2, the first holding plate 212, second holding plate 214, and casing 224 include a series of flow openings 230 around the periphery of the components. Similarly, in the embodiment of FIG. 1, the first casing 22, first plate 12, second plate 14, and second casing 24 all include a series of flow openings 30 around the periphery of each component. Of course, in those embodiments in which the clamping mechanism does not span the width of the holding plates, the clamping mechanism need not include flow openings that match those of the holding plates. These flow openings can provide for flow across the tissue holder during a procedure. For instance, if the primary openings 16, 17 contain a tissue that either blocks flow completely or allows partial or periodic flow (e.g., a heart valve), the flow openings can be used to control pressure across the tissue. During assembly of a device, the flow openings 30 can be partially or fully aligned to allow a controllable flow through the openings or can be purposely misaligned to limit or prevent flow through the flow openings. Alternatively, the tissue holder can include an O-ring that can be assembled with the device (e.g., external to one of the casings) that can completely block flow through the flow openings. In this embodiment, all flow through the device will be forced through the primary openings 16, 17 and the tissue held there (e.g., through a heart valve) or alternatively, there can be no flow through the device, with a tissue held in the openings 16, 17 blocking any flow through the primary openings 16, 17.

Figure 3:
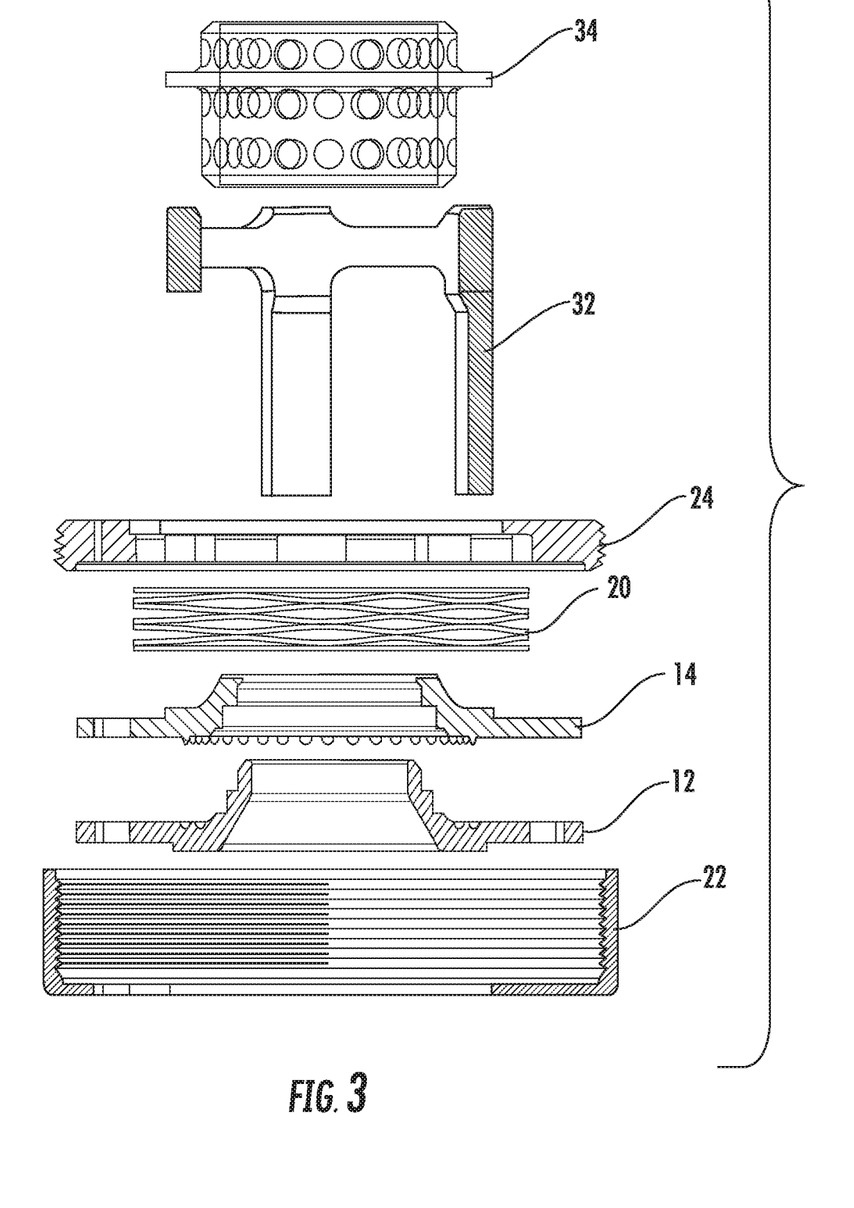
FIG. 3 is an exploded view of the tissue holder of FIG. 1.
Figure 6:
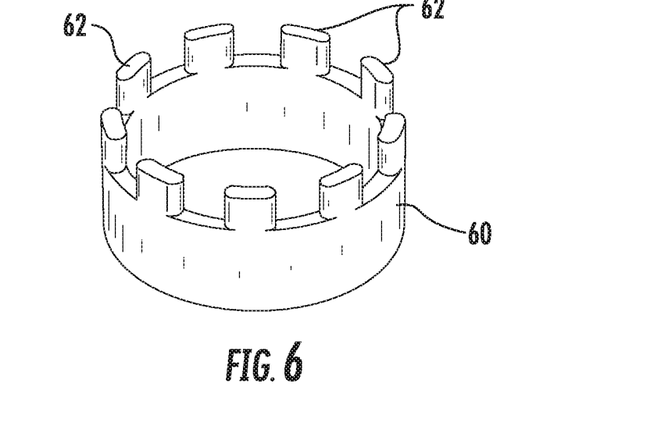
FIG. 6 illustrates a tightening/temporary support tool for use with a device.
Figure 7:
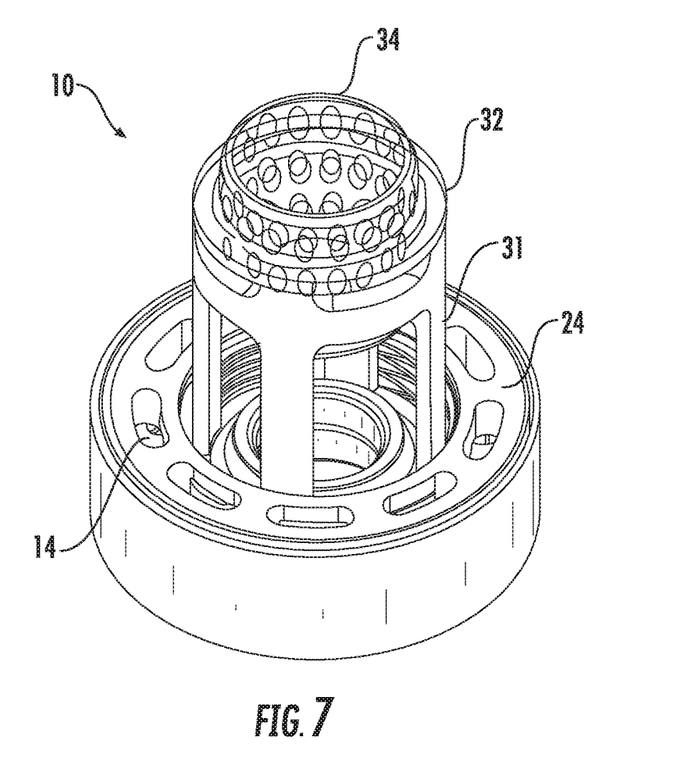
FIG. 7 is a schematic of a perspective view of an assembled tissue holder.

The flow openings can also be utilized for tightening the clamping mechanism of the tissue holder. In one embodiment, the tissue holder can include a tool 60 as illustrated in FIG. 6. The tool 60 can include a series of teeth 62 that can fit into the flow openings 30 of the casing 24 (FIG. 7). The tool 60 can be, e.g., injection molded, 3D printed, etc., and can facilitate tightening of the clamping mechanism during assembly of the tissue holder. In addition, the tool 60 can support the tissue to be held in the device during assembly. The teeth 62 on the tool 60 can be designed with a predetermined height to selectively control which plates of the device are tightened by the tool. For instance, the teeth 62 can be relatively short, and during use the tool 60 can tighten only the upper casing 24 of a device as illustrated in FIG. 1, FIG. 3 and FIG. 7. In this embodiment, the tool will not place any circumferential forces on the tissue held between the first and second plates. Alternatively, the tool 60 can include longer teeth 62 that can reach through the flow holes of the upper casing and engage with the flow holes of the second plate 14, which can place a torqueing force on the tissue held between the plates. In yet another alternative embodiment, the teeth 62 of the tool 60 can reach through the flow holes of both the first plate 14 and the second plate 12 and even through the flow holes of the first casing 22 to align the flow holes and/or to rotate the entire device 10 to a desired orientation in a secondary device (e.g., in a decellularization device).

The tissue holder can be designed for gripping heart valve tissue. In this embodiment, the tissue can be held such that the valve itself is suspended in or near the aligned primary openings of the first and second plates that are held together with the clamping mechanism and screw. In one embodiment, a heart valve tissue segment may include at least a segment of a valve root (e.g. an aortic root in the case of an aortic valve) in conjunction with the heart valve. For such embodiments, the tissue holder can include a stand and a containment aide for supporting the valve root. FIG. 7 illustrates one embodiment of a tissue holder 10 following assembly. The stand 32 can include multiple feet 31 that can be attachable to some other component of the tissue holder such as a casing or a holding plate. For instance, one or more feet 31 can be removably attachable to the second holding plate 14 of the tissue holder. The attachment between the stand 32 and the second holding plate 14 can be any suitable attachment, such as a ridged snap-lock, a luer-lock type of fitting, a key-hole fitting, or the like.

The containment aide 34 can be separable from the stand 32 as shown in FIG. 2 and FIG. 3 or the two can be of unitary construction, as desired. For instance, the containment aide 34 can simply snap into place on the distal end of the stand 32 via a ridged snap lock, a key-hole fitting, or the like. Optionally, the containment aide 34 can be adjustable on the stand 32 so as to accommodate different heights of a valve root. For instance, the containment aide 34 can include telescoping components that can be used to increase or decrease the height of the containment aide 34. The containment aide 34 can include components for containing the tissue on/in the stand. For example, in one embodiment the containment aide 34 can include holes that can be utilized to suture a tissue segment to the containment aide. Alternatively, a tissue segment can be clipped, tied, or otherwise contained on the aide and thus more securely held to the stand 32.

FIG. 3 presents an exploded image of the tissue holder 10 including the first casing 22 and the second casing 24 that can be attached to one another as a clamping mechanism for the device. Also shown is the first holding plate 14 and the second holding plate 12 between which a tissue portion can be secured, as well as a stand 32 and a containment aide 34 that can be utilized to hold a vessel portion, such as a valve root.

Figure 8:
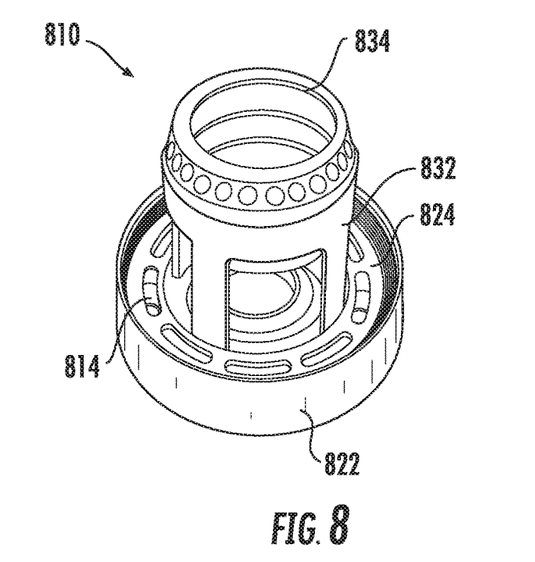
FIG. 8 is an image of an assembled tissue holder.

FIG. 8 is another image of a tissue holder 810 following assembly. As can be seen, the tissue holder 810 includes a first casing 822 and a second casing 824 that are threaded together to form a clamping mechanism that holds the first holding plate (not visible in FIG. 8), the second holding plate 814, and the spring (not visible in FIG. 8) there between. The tissue holder 810 also includes a stand 832 and a suture aide 834 that can be used to support a valve root of a section of heart valve tissue.

Figure 9:
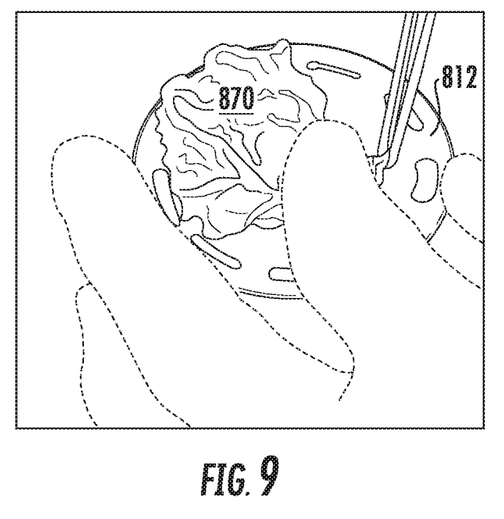
FIG. 9 illustrates the placement of a tissue portion on one side of a holding plate.
Figure 10:
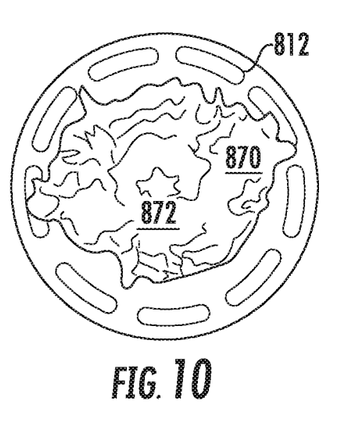
FIG. 10 illustrates the holding plate following location of the tissue portion on the holding plate.

FIG. 9 illustrates a method for associating a tissue with a tissue holder. As can be seen a tissue section 870 can be spread over a surface of a first plate 812 of the holder. It should be understood that there is no requirement as to which of the two holding plates the tissue contacts first, the tissue will be applied to one surface of one of the plates and the second plate will then be aligned with the first plate such that the two primary openings are axially aligned. In FIG. 10, the tissue 870 has been spread over the surface of the plate 812 and is ready for the second plate to be aligned with the plate 812. In this embodiment, the tissue 870 includes a heart valve 872 that is located near or within the primary opening of the plate 812.

Figure 11:
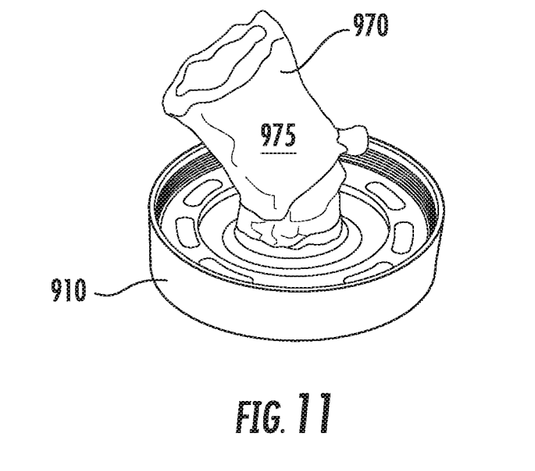
FIG. 11 illustrates heart valve tissue gripped by a tissue holder.
Figure 12:
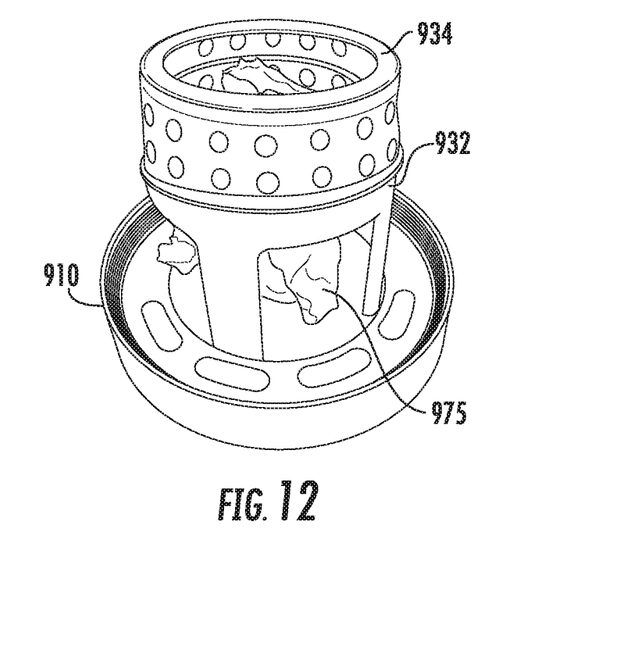
FIG. 12 illustrates an assembled device that is holding a heart valve and associated tissue.

FIG. 11 illustrates the assembled tissue holder 910 with a section of heart valve tissue 970 in the holder. In this figure, the valve root 975 has not yet been attached to a stand of the holder. In FIG. 12, the stand 932 and containment aide 934 have been attached to the tissue holder 910 and the valve root 975 is held inside of the stand 932. The valve root 975 can then be attached to the containment aide 934 and more firmly held during subsequent testing/procedures. A section of the ventricle tissue (not visible in FIG. 11 or FIG. 12) is clamped between the plates for gripping the heart valve tissue 970 as discussed previously.

Figure 13A:
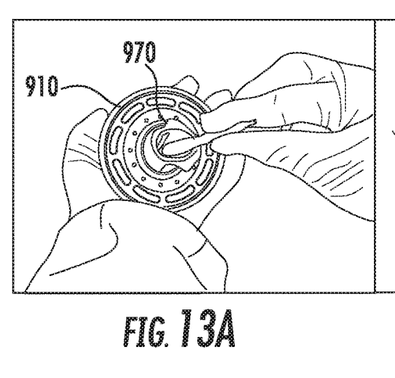
Figure 13B:
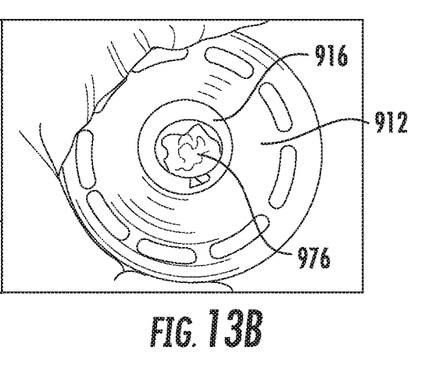

FIG. 13 illustrates a top view (FIG. 13A) and a bottom view (FIG. 13B) of the assembled tissue holder 910 with the heart valve tissue 970 gripped in the holder. As can be seen, the heart valve 976 is accessible in the primary opening 916 of the first holding plate 912 from both the top via the valve root (FIG. 13A) and from the bottom (FIG. 13B).

Figure 14:
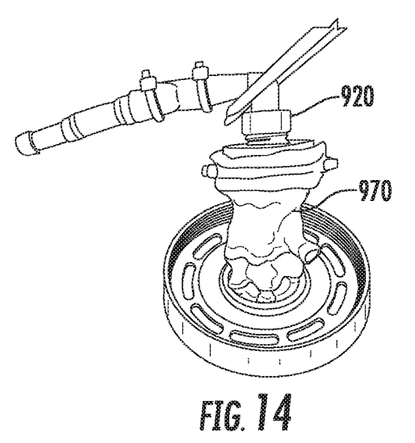
FIG. 14 illustrates a heart valve and associated tissue held in a device and coupled with a capping device.
Figure 15:
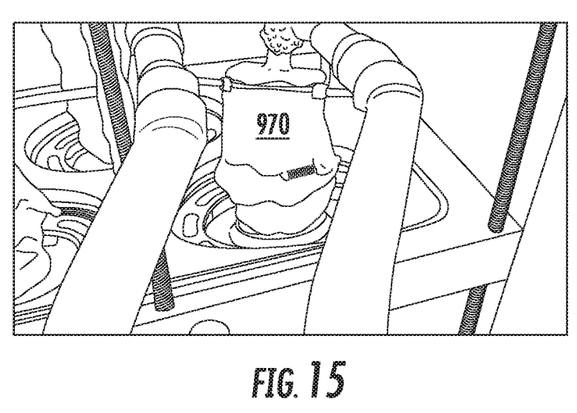
FIG. 15 illustrates a heart valve and associated tissue held in a treatment system for treating the tissue.

The tissue that is gripped in the tissue holder can be subjected to one or more treatment protocols and can be firmly gripped by the tissue holder throughout the protocols. In one embodiment, the tissue holder can enable completely hands-free manipulation of a tissue from excisement or development to implantation. For instance, the engineered or excised tissue can be subjected to multiple treatment protocols that utilize multiple different devices and systems without the need to remove the tissue from the holder. For instance, in FIG. 14 the heart valve tissue 970 has been connected to a capping device 920 with an outflow tube that can be located in a decellularization chamber as illustrated in FIG. 15. Following this treatment protocol, the tissue holder can be removed from the system and moved to a second system for further treatment of the tissue, and the tissue can remain in the holder without further handling of the tissue itself.

It will be appreciated that the foregoing examples, given for purposes of illustration, are not to be construed as limiting the scope of this disclosure. Although only a few exemplary embodiments of the disclosed subject matter have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. A tissue holder comprising:
a first holding plate having a first side and a second side and defining a primary opening therethrough that passes from the first side of the first holding plate to the second side of the first holding plate, the primary opening of the first holding plate defining a first central axis therethrough;
a second holding plate having a first side and a second side and defining a primary opening therethrough that passes from the first side of the second holding plate to the second side of the second holding plate, the primary opening of the second holding plate defining a second central axis therethrough, the second holding plate being alignable with the first holding plate such that upon alignment of the first and second holding plates the second side of the first holding plate is adjacent to the first side of the second holding plate and the first and second central axes are aligned with one another and the primary openings of the first and second holding plates are axially aligned with one another;

a clamping mechanism, the clamping mechanism being capable upon assembly of the tissue holder of applying a clamping force between the first side of the first holding plate and the second side of the second holding plate with when the first and second holding plates are aligned with one another; and a spring capable of being held between the clamping mechanism and either the first holding plate or the second holding plate, wherein the spring is a coil spring, a leaf spring, or a wave spring, the spring having a compression force direction, the spring being configured such that upon assembly of the tissue holder the compression force direction of the spring is parallel to the aligned first and second central axes of the first and second holding plates.

2. The tissue holder of claim 1, the first holding plate further comprising one or more three dimensional features on the second side of the first holding plate.

3. The tissue holder of claim 2, the second holding plate further comprising one or more three dimensional features on the first side of the second holding plate that engage with the three dimensional features of the first holding plate.

4. The tissue holder of claim 1, wherein the clamping mechanism includes a first casing having a threaded surface.

5. The tissue holder of claim 4, wherein the first holding plate includes a threaded surface that pairs with the threaded surface of the first casing.

6. The tissue holder of claim 4, the clamping mechanism further comprising a second casing having a threaded surface that pairs with the threaded surface of the first casing.

7. The tissue holder of claim 1, further comprising one or more additional holding plates, the one or more additional holding plates each having a primary openings, the primary openings of the additional holding plates having a cross sectional dimension and/or shape that is different from a cross sectional dimension and/or shape of the primary opening of the first holding plate and/or the primary opening of the second holding plate, the one or more additional holding plates being configured for assembly in the tissue holder alternative to the first and/or second holding plates of the tissue holder.

8. The tissue holder of claim 1, the first holding plate and the second holding plate further defining one or more flow openings.

9. The tissue holder of claim 8, further comprising a tool that engages with at least a portion of the flow openings.

10. The tissue holder of claim 1, the tissue holder further comprising a stand capable of attachment to the tissue holder, the stand extending from the primary opening of the first holding plate or the second holding plate in the direction of the first and second central axes upon assembly of the tissue holder.

11. The tissue holder of claim 10, further comprising a containment aide attachable to the stand.

12. The tissue holder of claim 1, wherein the tissue holder is removably attachable to one or more systems for treating a tissue.

* * * * *